US012788788B2

(12) United States Patent
Speckmann et al.

(10) Patent No.: US 12,788,788 B2
(45) Date of Patent: Nov. 10, 2026

(54) PROBIOTIC COMPOSITION FOR GUT MICROBIOME MODULATION

(71) Applicant: Evonik Operations GmbH, Essen (DE)

(72) Inventors: Bodo Speckmann, Kahl (DE); Marco Gobbetti, Bozen-Bolzano (IT); Helga Carola Pankoke, Bielefeld (DE); Monika Flügel, Steinhagen (DE); Lorena Stannek-Göbel, Bielefeld (DE); Heike tom Dieck, Friedrichsdorf (DE)

(73) Assignee: Evonik Operations GmbH, Essen (DE)

( * ) Notice: Subject to any disclaimer, the term of this patent is extended or adjusted under 35 U.S.C. 154(b) by 274 days.

(21) Appl. No.: 18/704,505

(22) PCT Filed: Oct. 25, 2022

(86) PCT No.: PCT/EP2022/079755
§ 371 (c)(1),
(2) Date: Apr. 25, 2024

(87) PCT Pub. No.: WO2023/072921
PCT Pub. Date: May 4, 2023

(65) Prior Publication Data

US 2025/0000920 A1 Jan. 2, 2025

(30) Foreign Application Priority Data

Oct. 26, 2021 (EP) .................................... 21204680

(51) Int. Cl.
*A61K 35/747* (2015.01)
*A61K 35/00* (2006.01)
*A61K 35/742* (2015.01)
*A61P 1/14* (2006.01)

(52) U.S. Cl.
CPC .......... *A61K 35/747* (2013.01); *A61K 35/742* (2013.01); *A61P 1/14* (2018.01); *A61K 2035/115* (2013.01)

(58) Field of Classification Search
CPC ................ A61K 35/747; A61K 35/742; A61K 2035/115; A61K 35/741; A61K 35/744; A61K 2300/00; A61P 1/14; A61P 1/00; A61P 37/06; A61P 43/00; A23L 33/135; A23V 2002/00; A23V 2200/32; A23V 2400/11; A23V 2400/41
See application file for complete search history.

(56) References Cited

U.S. PATENT DOCUMENTS 10,265,349 B2 * 4/2019 Chatila ................ A61K 35/741
11,173,184 B2 11/2021 Petri et al.
2017/0340683 A1 11/2017 Petri et al.
2020/0113952 A1 4/2020 Pelzer et al.
2021/0392935 A1 12/2021 Speckmann et al.
2022/0088091 A1 3/2022 Ochrombel et al.
2022/0168363 A1 6/2022 Stannek-Göbel et al.
2023/0128187 A1 4/2023 Speckmann et al.
2023/0270137 A1 8/2023 Borchers et al.

FOREIGN PATENT DOCUMENTS

WO 2021/129997 7/2021
WO 2021/129998 7/2021

OTHER PUBLICATIONS

Zhao et al., Gut bacteria selectively promoted by dietary fibers alleviate type 2 diabetes. Science. Mar. 9, 2018;359(6380): 1151-1156. doi: 10.1126/science.aao5774. PMID: 29590046. (Year: 2018).*

Castellazzi AM, Valsecchi C, Caimmi S, Licari A, Marseglia A, Leoni MC, Caimmi D, Miraglia del Giudice M, Leonardi S, La Rosa M, Marseglia GL. Probiotics and food allergy. Ital J Pediatr. Jul. 29, 2013;39:47. doi: 10.1186/1824-7288-39-47. PMID: 23895430; PMCID: PMC3733627. (Year: 2013).*

Xu et al., Front. Microbiol., Oct. 8, 2018, Sec. Infectious Agents and Diseasevol. 9—2018, doi.org/10.3389/fmich.2018.02396 (Year: 2018).*

U.S. Appl. No. 16/627,195, filed Dec. 27, 2019, 2017/0113952, Pelzer et al.

U.S. Appl. No. 17/049,155, filed Oct. 20, 2020, 2022/0088091, Ochrombel et al.

U.S. Appl. No. 17/296,465, filed May 24, 2021, 2021/0392935, Speckmann et al.

U.S. Appl. No. 17/429,905, filed Aug. 10, 2021, 2022/0168363, Stannek-Göbel et al.

U.S. Appl. No. 18/279,388, filed Aug. 30, 2023, Speckmann et al.

U.S. Appl. No. 17/788,239, filed Jun. 22, 2022, 2023/0128187, Speckmann et al.

U.S. Appl. No. 18/251,343, filed May 1, 2023, 2023/0270137, Borchers et al.

U.S. Appl. No. 18/702,912, filed Apr. 19, 2024, Dieck et al.

De Angelis et al, "Selection of Gut-Resistant Bacteria and Construction of Microbial Consortia for Improving Gluten Digestion under Simulated Gastrointestinal Conditions", Nutrients, vol. 13, No. 992, Mar. 19, 2021, pp. 1-18.

(Continued)

*Primary Examiner* — Kade Ariani
(74) *Attorney, Agent, or Firm* — Grüneberg Global IP, PLLC

(57) ABSTRACT

Preparations can be used for treating or preventing dysbiosis in humans and animals. The preparation has the probiotic strains *Lactobacillus plantarum* DSM 33363, *Lactobacillus plantarum* DSM 33364, *Lactobacillus paracasei* DSM 33373, *Lactobacillus reuteri* DSM 33374, *Bacillus megaterium* DSM 33300, *Bacillus pumilus* DSM 33297, and *Bacillus pumilus* DSM 33355. The preparation can be used for the modulation of the composition and activity of gut microbiota

19 Claims, 2 Drawing Sheets

Specification includes a Sequence Listing.

(56) References Cited

OTHER PUBLICATIONS

Francavilla et al, "Clinical and Microbiological Effect of a Multispecies Probiotic Supplementation in Celiac Patients With Persistent IBS-type Symptoms : A Randomized, Double-Blind, Placebo-controlled, Multicenter Trial", J. Clin. Gastroenterol., vol. 53, No. 3, Mar. 1, 2019, pp. e117-e125.
International Search Report received for PCT Application No. PCT/EP2022/079755, mailed on Feb. 1, 2023, 7 pages.
Written Opinion received for PCT Application No. PCT/EP2022/079755, mailed on Feb. 1, 2023, 11 pages.

* cited by examiner

PROBIOTIC COMPOSITION FOR GUT MICROBIOME MODULATION

CROSS-REFERENCE TO RELATED APPLICATIONS

This application is a National Stage entry under § 371 of International Application No. PCT/EP2022/079755, filed on Oct. 25, 2022, and which claims the benefit of priority to European Patent Application No. 21204680.9, filed on Oct. 26, 2021. The content of each of these applications is hereby incorporated by reference in its entirety.

DEPOSIT OF BIOLOGICAL MATERIAL

The following microorganisms were deposited with Leibniz Institute DSMZ-German Collection of Microorganisms and Cell Cultures having an address at Inhoffenstr. 7 B D-38124 Braunschweig under the Budapest Treaty on the International Recognition of the Deposit of Microorganisms for the Purposes of Patent Procedure. A description of the microorganism, date of deposit and accession number are provided as follows: *Lactobacillus plantarum* DSM 33363 (date of deposit Dec. 5, 2019), *Lactobacillus plantarum* DSM 33364 (date of deposit Dec. 5, 2019), *Lactobacillus paracasei* DSM 33373 (date of deposit Dec. 10, 2019), *Lactobacillus reuteri* DSM 33374 (date of deposit Dec. 10, 2019), *Bacillus megaterium* DSM 33300 (date of deposit Oct. 17, 2019), *Bacillus pumilus* DSM 33297 (date of deposit Oct. 17, 2019), *Bacillus pumilus* DSM 33355 (date of deposit Dec. 3, 2019) and *Pediococcus pentosaceus* DSM 33371 (date of deposit Dec. 5, 2019).

REFERENCE TO A SEQUENCE LISTING

The present application is accompanied by an XML file as a computer readable form containing the sequence listing entitled, "006026USPCT-seqlist-as-filed.xml", created on Apr. 1, 2024, with a file size of 2,614 bytes, the content of which is hereby incorporated by reference in its entirety.

BACKGROUND OF THE INVENTION

Field of the Invention

The current invention concerns the use of preparations for treating or preventing dysbiosis in humans and animals, wherein the preparation comprises the probiotic strains *Lactobacillus plantarum* DSM 33363, *Lactobacillus plantarum* DSM 33364, *Lactobacillus paracasei* DSM 33373, *Lactobacillus reuteri* DSM 33374, *Bacillus megaterium* DSM 33300, *Bacillus pumilus* DSM 33297, and *Bacillus pumilus* DSM 33355.

Description of Related Art

An increasing number of health disorders (including diabetes, allergic & autoimmunity diseases, cancers, inflammatory bowel diseases, brain disorders) have been linked to a dysfunctional gut microbiome [1]. This link appears to be bidirectional, and therefore microbiota-targeted strategies have been conceived as novel therapeutic opportunities to prevent or treat these disorders. The gut microbiome affects human and animal physiology via e.g. soluble factors deriving from microbial metabolism, modulation of local and systemic immune cells, modulation of the enteric nervous system and the vagus nerve. On the other hand, gut microbiota composition and activity are affected by intrinsic (genome, sex, age, diseases) and a multitude of extrinsic factors, with diet being probably the most important determinant. Dietary modulation of the microbiota's composition and activity includes the application of prebiotics, probiotics, synbiotics, and antibiotics. The most investigated and commercially available probiotics are mainly microorganisms from species of genera *Lactobacillus* and *Bifidobacterium.*

Dysbiosis has been described for subjects with food intolerances, e.g. towards histamine [2] and gluten [3]. Evaluations of the fecal and/or duodenal gut microbiota composition in celiac disease (CD) patients versus healthy controls revealed reduced alpha diversity, increased levels of Proteobacteria, the genera *Bacteroides, Prevotella, Escherichia, Pseudomonas, Neisseria, Serratia*, and *Haemophilus*, and decreased levels of *Streptococcus, Akkermansia*, Bifidobacteria and Lactobacilli [3-6]. An increased abundance of Proteobacteria-*Neisseria* spp. in particular—has recently been confirmed to occur in the salivary, duodenal, and fecal microbiota of CD patients [7-9].

CD patients' dysbiosis may develop during the course of disease and in that sense rather have a bystander role; other studies do however indicate that dysbiosis precedes CD development and can act as an exacerbator of the disease [10]. This view has been supported by functional analyses of prevalent species in the dysbiotic human gut microbiota (e.g. *Neisseria flavescens* and *Pseudomonas aeruginosa*) [6,8]. Likewise, an *Escherichia coli* ENT CAI: 5 strain that was isolated from a CD patients' fecal sample aggravated gluten-induced immunopathology in clean SPF mice [11]. Human digestive proteases only partially digest proline-rich gliadins. In general, this incapability limits digestive processes and leads to the genesis of gluten-derived peptides (epitopes) which act as triggering factors for celiac disease in susceptible individuals [12]. *Neisseria flavescens* and *Pseudomonas aeruginosa* have the capability to increase the content of these epitopes [13], which efficiently cross the intestine mucosal barrier [14]. These features attribute a detrimental role for pathogens associated with dysbiosis in the etiology of celiac disease and possibly also other gluten-related disorders like non-celiac gluten sensitivity (NCGS). NCGS shares features with CD relating to symptoms and treatment (gluten-free diet) and is the second major manifestation in the spectrum of gluten-related disorders. There are few reports on gut microbiota composition in NCGS. These analyses are not only lower in number but also less clear compared to CD, given the less precise diagnosis of NCGS and its symptoms overlapping with irritable bowel syndrome. Nevertheless, the gut microbiota of NCGS patients typically displays reduced levels of Bifidobacteria and butyrate-producing Firmicutes [15,16], increased Proteobacteria, *Actinobacillus*, and *Finegoldia levels and a decreased richness* [16]. The gluten-free diet (GFD) is the only available and thus mandatory treatment for both NCGS and CD patients. Its impact on gut microbiota composition has been studied for both diseases. Mexican NCGS patients responded to a GFD with higher abundances of Gammaproteobacteria and *Pseudomonas* [17]. Other studies reported decreases in *Bacteroides, Blautia, Dorea, Coprococcus, Collinsella*, Lachnospiraceae, and increased Bacteroidaceae in GFD-treated NCGS [18]. CD patients' microbiota composition is also (negatively) affected by GFD, with reported increases in Proteobacteria, *Pseudomonas, Prevotella*, and *Streptococcus* species, whereas diversity and abundance of Lactobacillii and Bifidobacteria apparently decrease [18]. As the GFD is the only currently available treatment for CD patients, its disadvantageous side-effects consequentially show the urgent need for novel microbiome-modulating (co-) treatment strategies.

The GFD has gained popularity also beyond those affected by gluten-related disorders, and it is now one of the most sought-after exclusion diets [19], though it poses disadvantages and potential harms especially to healthy people [20]. Effects of GFD and diets with low gluten content (up to 2 g per day) on abundance of bacterial populations in healthy people have been studied and summarized [18]. Overall, gluten exclusion results in depletion of Bifidobacteria, Lactobacillii, *Faecalibacterium prausnitzii, Dorea* species (e.g. *Dorea longicatena*), *Blautia wexlerae*, Veillonellaceae, *Roseburia*, Anaeostipes *hadrus, Eubacterium hallii*, and expansion of *E. coli, Slackia*, Enterobacteriaceae, Coriobacteriaceae, and Proteobacteriaceae [18,21,22].

In summary, gut dysbiosis is associated with an increasing number of pathologic conditions including food intolerances, and while the cause-and-effect relationship is often unclear, the discovery of modes of actions of some differentially prevalent taxa has indicated that dysbiosis can be a disease driver that is worthwhile to be targeted. Attempts have been made to correct dysbiosis in different contexts, most often by application of pre-, pro-, and synbiotics, but the limitation of currently available microbiome-modulating interventions is their lack of accuracy and unclear clinical effectiveness.

Under WO/2021/129998 and we previously disclosed various combinations of strains of the genera *Bacillus* and *Lactobacillus* and their capabilities to digest gluten completely. However, prebiotic or microbiome-modulating effects of these strains and combinations thereof—which is the subject of this invention—have not been disclosed anywhere before.

Francavilla et al. reported increased abundances of presumptive lactic acid bacteria, *Staphylococcus* and *Bifidobacterium* in the stools of CD patients upon six-week treatment with a composition comprising the bacterial strains *Lactobacillus casei* LMG 101/37 P-17504, *Lactobacillus plantarum* CECT 4528, *Bifidobacterium animalis* subsp. *lactis* Bi1 LMG P-17502, and *Bifidobacterium breve Bbr*8 LMG P-17501 [23]. The application of other strains of the genus *Bifidobacterium* (*B. breve, B. longum*) for confined effects on the gut microbiota has been summarized, including modulation of the amounts of Firmicutes, Bacteroidetes, *Bacteroides fragilis*, without further assessments of the taxa comprising these groups.

SUMMARY OF THE INVENTION

We disclosed previously a multi-strain probiotic composition that completely hydrolyzes gluten to non-toxic and non-immunogenic digests (PCT/EP2020/083770, [12]). Surprisingly, we discovered that this composition leads to beneficial changes in the gut microbiome of humans on the background of a gluten-free and a controlled gluten-containing diet that have not been disclosed for this or any other composition before. These changes included an unprecedented modulation of several taxa previously linked to gluten-related disorders and the gluten-free diet. Our discovery of prebiotic functions of this multi-strain probiotic formulation paves the way for novel strategies to prevent, treat and/or cure disorders and pathologies linked to a dysfunctional microbiome, in particular for humans and animals adhering to a gluten-free or gluten-reduced diet, or suffering from celiac disease and similar gluten-related disorders.

Therefore, the present invention is directed to the use of a preparation for treating or preventing dysbiosis in humans and animals, wherein the preparation comprises *Lactobacillus plantarum* DSM 33363, *Lactobacillus plantarum* DSM 33364, *Lactobacillus paracasei* DSM 33373, *Lactobacillus reuteri* DSM 33374, *Bacillus megaterium* DSM 33300, *Bacillus pumilus* DSM 33297, and *Bacillus pumilus* DSM 33355.

The strains were already disclosed in the patent application WO2021129998A1.

DETAILED DESCRIPTION OF THE INVENTION

Figure 1:
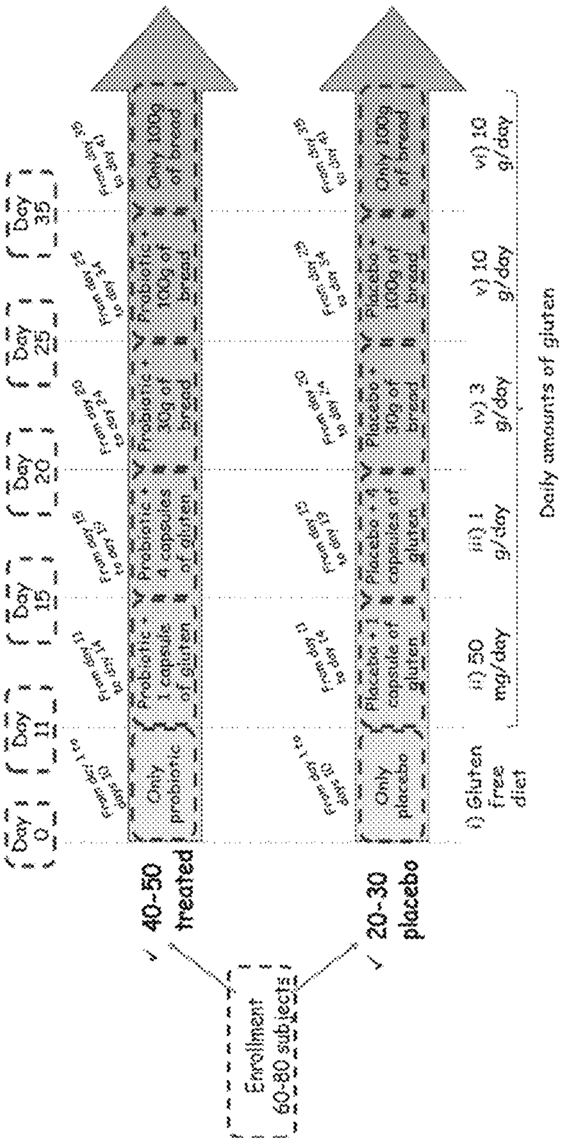
FIG. 1 shows the illustration of the trial setup.

In a preferred embodiment, the modulation of the composition and activity of gut microbiota is selected from one or more of a) the preparation leads to an increase of taxa belonging to *Bifidobacterium, Lactobacillus, Akkermansia muciniphila, Streptococcus, Faecalibacterium prausnitzii* b) the preparation leads to a decrease of taxa belonging to Proteobacteria, *Neisseria, Neisseria flavescens, Escherichia coli, Bordetella, Shigella, Salmonella, Bacteroides, Prevotella, Helicobacter pylori, Yersinia, Pseudomonas, Pseudomonas aeruginosa, Klebsiella* c) the preparation leads to an increased alpha or beta diversity as well as an increased evenness of the gut microbiota.

In a specific configuration, the preparation leads to a relative increase of at least 5% of taxa belonging to *Bifidobacterium, Lactobacillus, Akkermansia muciniphila, Streptococcus, Faecalibacterium prausnitzii* compared to the placebo group.

In another specific configuration, the preparation leads to a relative decrease of at least 5% of taxa belonging to Proteobacteria, *Neisseria, Neisseria flavescens, Escherichia coli, Bordetella, Shigella, Salmonella, Bacteroides, Prevotella, Helicobacter pylori, Yersinia, Pseudomonas, Pseudomonas aeruginosa, Klebsiella* compared to the placebo group.

In another specific configuration, the preparation leads to a relative increase of at least 5% of alpha or beta diversity as well as an increased evenness of the gut microbiota compared to the placebo group.

The cells of the strains of the current invention may be present in the compositions of the current invention, as spores (which are dormant), as vegetative cells (which are growing), as transition state cells (which are transitioning from vegetative cells to spores, or reverse), as cellular extracts or as a combination of at least two of these types of cells. In a preferred embodiment, the probiotic strain is present in a dormant form or as vegetative cells. In alternative embodiment, cytoplasmic extracts or cell-free supernatants or heat-killed biomass of the probiotic strains are used.

In a further preferred embodiment, the preparation further comprises one or more probiotic strains, preferably selected from *Pediococcus* sp., *Weissella* sp., more preferably *Pediococcus pentosaceus* DSM 33371.

In a further preferred embodiment, the preparation further comprises one or more of the following: microbial proteases purified from *Aspergillus niger, Aspergillus oryzae, Bacillus* sp., *Lactobacillus* sp., *Pediococcus* sp., *Weissella* sp., *Rothia mucilaginosa, Rothia aeria*, subtilisins, nattokinase, arabinoxylans, barley grain fibre, oat grain fibre, rye fibre, wheat bran fibre, inulins, fructooligosaccharides (FOS), galactooligosaccharides (GOS), resistant starch, beta-glucans, glucomannans, galactoglucomannans, guar gum, xylooligosaccharides, alginate.

The invention is also directed to use of preparations for correcting the dysbiosis typically occurring on the background of or preceding the development of gluten-related disorders, preferably selected from celiac disease, non-celiac gluten sensitivity, wheat allergy, and gluten-sensitive irritable bowel syndrome in a subject or animal in need thereof.

In a preferred configuration, the preparation is for treating or preventing dysbiosis that derives from adhering to special dietary practices including gluten-free diets, diets with reduced intake of gluten or cereals or cereal-derived or -containing food stuffs.

Moreover, the preparation is for treating or preventing dysbiosis, preferably dysbiosis related to type two diabetes, obesity, non-alcoholic fatty liver disease, allergic diseases, major depressive disorder, Parkinson's disease, Alzheimer's disease, auto-immune diseases.

In a preferred embodiment, the preparation further comprises a substance, which acts as permeabilizer of the microbial cell membrane of members of *Bacillus* sp., *Lactobacillus* sp., *Pediococcus* sp., *Weissella* sp., preferably alginate.

In an alternative embodiment, one or more of the probiotic strains selected from *Bacillus* sp., *Lactobacillus* sp., *Pediococcus* sp. and *Weissella* sp. are immobilized individually or as consortia. Immobilization can be realized on solid surfaces such as cellulose and chitosan, as entrapment within a porous matrix such as polysaccharide gels like alginates, k-carrageenan, agar, chitosan and polygalacturonic acid or other polymeric matrixes like gelatin, collagen and polyvinyl alcohol or by flocculation and microencapsulation or electrospraying technologies.

One subject of the present invention is the use of a preparation according to the present invention wherein the preparation is a food or feed supplement or functional food or food product or pharmaceutical product. Preferred foodstuffs according to the invention are chocolate products, gummies, mueslis, muesli bars, and dairy products.

A further subject of the current invention is also the use of a preparation of the current invention as a synbiotic ingredient in food products.

A further subject of the present invention is the use of the preparation as foodstuff composition further comprising at least one further food ingredient, preferably selected from proteins, carbohydrates, fats, further probiotics, prebiotics, enzymes, vitamins, immune modulators, milk replacers, minerals, amino acids, coccidiostats, acid-based products, medicines, and combinations thereof.

In a specific configuration, the preparation is formulated for oral use, preferably as pills, capsules, tablets, granular powders, opercula, soluble granules, bags, pills or drinkable vials, or is formulated as syrup or beverage, or is added to food, preferably cereals, gummies, bread, muesli, muesli bars, health bars, biscuits, chocolates, yoghurts or spreads.

The foodstuff composition according to the present invention does also include dietary supplements, e. g. in the form of a pill, capsule, tablet, powder, or liquid.

A further subject of the current invention is the use of the preparation as pharmaceutical composition containing a preparation according to the present invention and a pharmaceutically acceptable carrier.

WORKING EXAMPLES

Example 1: Gluten Challenge Trial Outline

FIG. 1 shows the illustration of the trial setup: treatment groups received either *verum* or placebo capsules for 34 days, while adhering to a gluten-free diet from day 1 to day 41 and receiving from day 11 onwards defined doses of gluten in the form of capsules or bread, escalating from 50 mg to 10 g of gluten per day.

FIG. 1 describes the outline of the human gluten challenge trial. Healthy human individuals aged 18-50 years were divided into two arms: (i) 40-50 subjected to probiotics administration, and (ii) 20-30 subjected to placebo. Probiotic or placebo capsules were ingested from day 1 to day 41 of the trial. Both arms adhered to a gluten-free diet for the first ten days to eliminate residual traces of gluten and similar proteins from the fecal material. After ten days, the gluten administration started for both arms as follows (shown in FIG. 1): 50 mg/day (capsules of gluten) for four days; 1 g/day (capsules of gluten) for four days; 3 g/day (reintroducing an equivalent amount of bread slides) for four days; and 10 g/day (reintroducing an equivalent amount of bread slides) for 17 days. This last dose of gluten corresponds to the average intake of gluten in most of the European countries. At this stage (10+4+4+4+10 +7 days=total of 41 days), the administration of the *verum* and placebo preparations were stopped, with a period of 7 days of wash-out. The wash-out period was included to provide information on the capability of the probiotics preparation to colonize for longer term in the gastrointestinal tract. The number of participants was calculated based on statistical power estimations to allow detection of statistically different effects comparing the *verum* and placebo groups. Fecal samples were collected at the beginning/end of each period for microbiological, gluten, immunological, and metabolome analysis.

Example 2: Effects of the Probiotic Formulation on Gut Microbiome Composition, Richness, and Alpha/Beta Diversity

TABLE 1

Comparison of fecal microbiota composition, richness, and alpha diversity of healthy adults

| Taxonomic group | Gluten-free diet | Gluten-reduced diet (50 mg per day) | Gluten-reduced diet (1000 mg per day) | "Normal" diet (10 g gluten/day) |
|---|---|---|---|---|
| *Proteobacteria* | ↓ | ↓ | ↓ | ↓ |
| *Neisseria* | ↓ | ↓ | ↓ | ↓ |
| *Neisseria flavescens* | ↓ | ↓ | ↓ | ↓ |

TABLE 1-continued

Comparison of fecal microbiota composition, richness, and alpha diversity of healthy adults

| | Gluten-free diet | Gluten-reduced diet (50 mg per day) | Gluten-reduced diet (1000 mg per day) | "Normal" diet (10 g gluten/day) |
|---|---|---|---|---|
| *Escherichia* | ↓ | ↓ | ↓ | ↓ |
| *Bordetella* | ↓ | ↓ | ↓ | ↓ |
| *Shigella* | ↓ | ↓ | ↓ | ↓ |
| *Salmonella* | ↓ | ↓ | ↓ | ↓ |
| *Bacteroides* | ↓ | ↓ | ↓ | ↓ |
| *Prevotella* | ↓ | ↓ | ↓ | ↓ |
| *Helicobacter* | ↓ | ↓ | ↓ | ↓ |
| *Yersinia* | ↓ | ↓ | ↓ | ↓ |
| *Pseudomonas* | ↓ | ↓ | ↓ | ↓ |
| *Pseudomonas aeruginosa* | ↓ | ↓ | ↓ | ↓ |
| *Klebsiella* | ↓ | ↓ | ↓ | ↓ |
| *Bifidobacteria* | ↑ | ↑ | ↑ | ↑ |
| *Lactobacilli* | ↑ | ↑ | ↑ | ↑ |
| *Akkermansia* | ↑ | ↑ | ↑ | ↑ |
| *Streptococcus* | ↑ | ↑ | ↑ | ↑ |
| *Faecalibacterium prausnitzii* | ↑ | ↑ | ↑ | ↑ |
| Other parameters: | | | | |
| Richness | ↑ | ↑ | ↑ | ↑ * |
| Alpha diversity | ↑ | ↑ | ↑ | ↑ |
| Observed OTU counts | ↑ | ↑ | ↑ | ↑ * |

Table 1: Comparison of fecal microbiota composition, richness, and alpha diversity of healthy adults receiving one capsule per day of a probiotic composition (*Lactobacillus plantarum* DSM 33363, *Lactobacillus plantarum* DSM 33364, *Lactobacillus paracasei* DSM 33373, *Lactobacillus reuteri* DSM 33374, *Bacillus megaterium* DSM 33300, *Bacillus pumilus* DSM 33297, and *Bacillus pumilus* DSM 33355) versus placebo capsules. *Verum* and placebo capsules were consumed on the background of diets with controlled content of gluten (gluten-free, 50 mg gluten, 1 g gluten, or 10 g gluten per day) as shown in FIG. 1 "↑" displays significantly increased abundance of the taxon in the probiotic group as compared to the placebo group; conversely for "↓". Exemplary parameters of fields indicated with an asterisk are shown in detail in FIG. 2.

Figure 2:
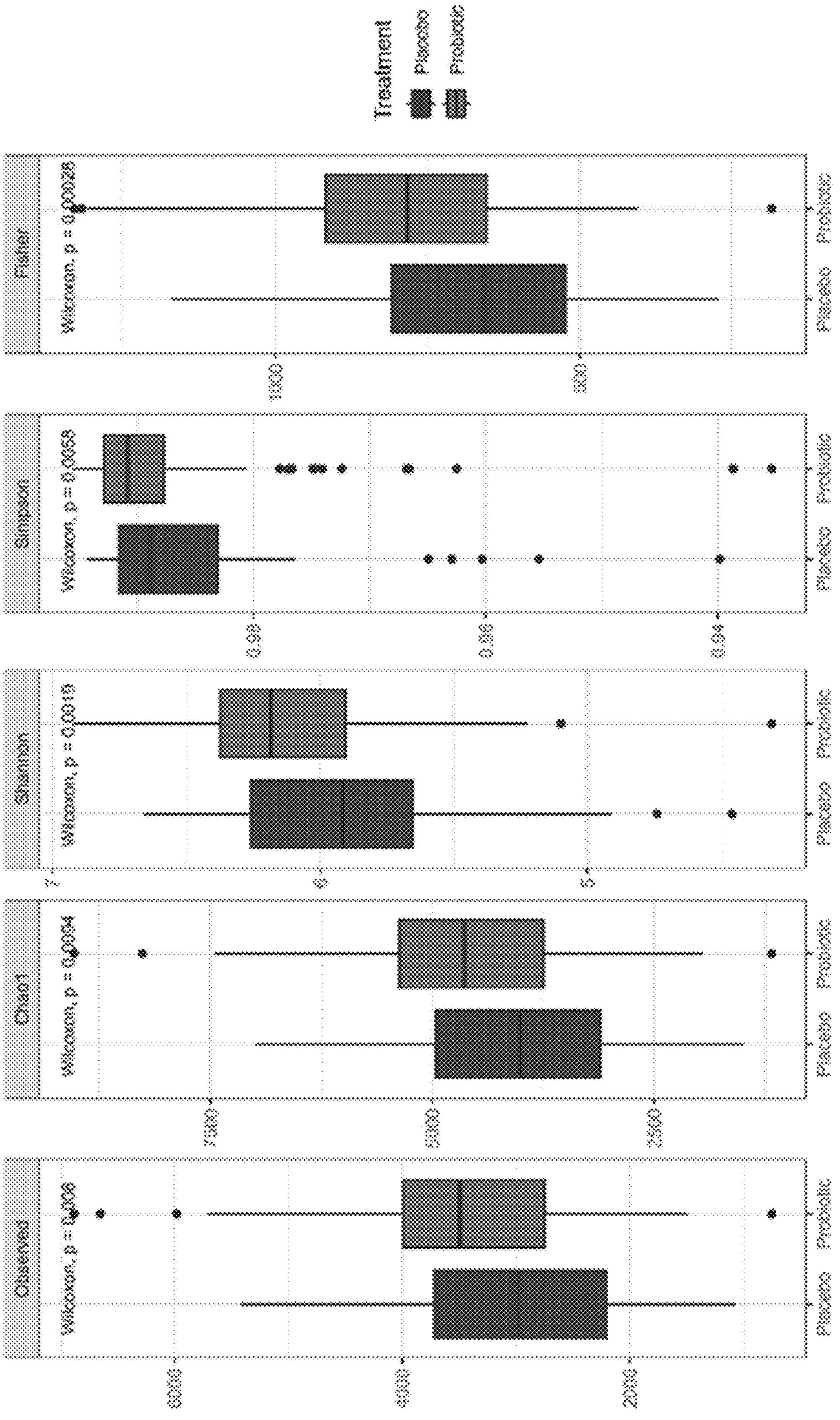
FIG. 2 shows the daily ingestion of a probiotic composition comprising *Lactobacillus plantarum* DSM 33363, *Lactobacillus plantarum* DSM 33364, *Lactobacillus paracasei* DSM 33373, *Lactobacillus reuteri* DSM 33374, *Bacillus megaterium* DSM 33300, *Bacillus pumilus* DSM 33297, and *Bacillus pumilus* DSM 33355 beneficially modulates gut microbiota composition.

FIG. 2 shows the daily ingestion of a probiotic composition comprising *Lactobacillus plantarum* DSM 33363, *Lactobacillus plantarum* DSM 33364, *Lactobacillus paracasei* DSM 33373, *Lactobacillus reuteri* DSM 33374, *Bacillus megaterium* DSM 33300, *Bacillus pumilus* DSM 33297, and *Bacillus pumilus* DSM 33355 beneficially modulates gut microbiota composition. Observed OTU counts and richness measures (Chao1, Shannon, Simpson and Fisher) between individuals that received probiotic (n=33) or placebo (n=11) treatment. Pairwise Wilcoxon signed-rank test was used to compare between means of the placebo and probiotic groups ($p<0.05$).

In addition to data shown in Table 1, abundances of *Bacillus*, Lacticaseibacillus, Lactiplantibacillus, Limosilactobacillus, Lacticaseibacillus *paracasei, Limosilactibacillus reuteri* were all higher in subjects supplemented with probiotic as compared to placebo. In conclusion, intake of the probiotic improved numerous microbial parameters that are reportedly impaired in gluten-related disorders and on the background of a gluten-free diet.

The analyses of fecal samples occurred through culture-dependent and culture-independent methods to estimate the survival of administered probiotics and, more in general, their effects on the gastrointestinal microbiota. Using the culture-dependent approach, selective media were used to quantify the viability of administered probiotics. A mixture of fecal samples (5 g) and 45 ml of sterilized physiological solution were homogenized. Relatively selective media were as follows:

MRS agar and Rogosa agar for presumptive *Lactobacillus;*

LBG agar for presumptive *Bacillus.*

RAPD-PCR analyses and partial sequencing of the 16S gene were performed to allow the identification of species/strains of the administered probiotics preparation from fecal material. Based on the genome sequences of the administered probiotics, the design of specific probes was performed using an RT-PCR analysis to confirm the fecal identification of *Lactobacillus plantarum* DSM 33363, *Lactobacillus plantarum* DSM 33364, *Lactobacillus paracasei* DSM 33373, *Lactobacillus reuteri* DSM 33374, *Bacillus megaterium* DSM 33300, *Bacillus pumilus* DSM 33297, and *Bacillus pumilus* DSM 33355For culture-independent analysis, RNA was extracted from an aliquot of ca. 200 mg of fecal sample using the Stool total RNA purification kit (Norgen Biotek Corp., Ontario, Canada, USA). Quality and concentration of RNA extracts was determined using 1% agarose-0.5×TBE gels and spectrophotometric measurements at 260, 280 and 230 nm through the NanoDrop ND-1000 Spectrophotometer. An aliquot of 1 μg of total RNA extracted was transcribed to cDNA using random examers and the Tetro cDNA synthesis kit from Bioline (Bioline USA Inc, Tanunton, MA, USA), according to the manufacturer instructions. Primers: forward primer 28F: GAGTTTGATCNTGGCTCAG and reverse primer 519R: GTNTTACNGCGGCKGCTG, based upon the V1-V3 region (*Escherichia coli* position 27-519) of the 16 S rRNA gene, was used to detect the fecal microbiome. cDNA sequencing analysis was performed on an Illumina platform. Raw sequence data were screened, trimmed and filtered with default settings, using the QIIME pipeline version 1.4.0 (http://qiime.sourceforge.net). Chimeras were excluded using B2C2 (http://www.researchandtesting.com/B2C2.html). Sequences with less than 250 bp were removed. FASTA sequences for each sample, without chimeras, were evaluated using BLASTn against a database derived from GenBank (http://ncbi.nlm.nih.gov). The sequences were first clustered into Operational Taxonomic Unit (OTU) clusters with 97% identity (3% divergence), using USEARCH. To determine the identities of bacteria, sequences were first queried, using a distributed BLASTn-.NET algorithm against a database of high-quality 16S bacterial sequences that derived from NCBI. Database sequences were characterized as high quality based on criteria, which were originally described by Ribosomal Database Project (RDP, v10.28). Alpha diversity (rarefaction, Good's coverage, Chao1 richness, Pielou's evenness and Shannon diversity indices) and beta diversity measures were calculated and plotted using QIIME. Final datasets at species and other relevant taxonomy levels will be compiled into separate worksheets for compositional analysis among the fecal samples and treatments.

Additionally, fecal samples were subjected to 16S rRNA gene amplification and sequencing as described [24]: for sequencing microbial composition, all fasting samples were analyzed by Biomes NGS GmbH (Wildau, Germany) via 16S rRNA gene amplification and sequencing. Microbial genomic DNA from fecal material was extracted by bead-beating technique. As the most promising for bacterial and archaeal primer pairs [25], the V3-V4 region of the 16S lRNA gene was amplified and sequencing was performed on the Illumina MiSeq platform using a 2×300 bp paired-end protocol, according to the manufacturer's instructions (Illumina, San Diego, CA, USA).

*Bioinformatics*

Raw microbial sequences were processed using the Quantitative Insights Into Microbial Ecology (QIIME) pipeline [26]. High-quality reads were binned into operational taxonomic units (OTUs) at a 97% similarity threshold using UCLUST and a "de novo" approach. Taxonomy was assigned using the Ribosomal Database Project (RDP) classifier against Greengenes database. All singleton OTUs were removed in an attempt to discard the majority of chimera sequences. Microbial alpha diversity was analyzed by using the Chao1 index, Shannon entropy, Simpson's index, and phylogenetic diversity whole tree metrics and beta diversity was estimated based on Bray-Curtis dissimilarity index and plotted as a multidimensional scaling or Principal Coordinates Analysis (PCoA) by the CLC Genomics Workbench version 20.0.4 (QIAGEN). The Mann-Whitney U test was used to analyze the mean difference of the alpha diversity index using GraphPad Prism version 9.0.0 (San Diego, CA, USA) and plotted as mean±SD. p-value <0.05 was considered statistically significant. The difference in the microbial community composition (beta diversity) of the groups was tested using the permutational multivariate analysis of variance (PERMANOVA).

Example 3: Effects of the Probiotic Formulation on Gut Microbiome Activity

To explore changes in the functional capacity of the intestinal microbiome between the *verum* (*Lactobacillus plantarum* DSM 33363, *Lactobacillus plantarum* DSM 33364, *Lactobacillus paracasei* DSM 33373, *Lactobacillus reuteri* DSM 33374, *Bacillus megaterium* DSM 33300, *Bacillus pumilus* DSM 33297, and *Bacillus pumilus* DSM 33355) and placebo group and in response to the dietary gluten intake, we analysed the trial participants' fecal 16S sequence data as described above. On the basis of marker gene sequencing profiles, we then predicted the functional potential of the bacterial communities with PICRUSt 2 and compared the results between the *verum* and placebo group for each dietary gluten regime. As shown in Table 2, probiotic intake increased the gut microbiome's capacity for protein degradation and carbohydrate metabolism, irrespective of the gluten intake.

TABLE 2

Comparison of PICRUSt2-predicted metabolic functions of fecal 16S rRNA microbiome data

| Metabolic function | Gluten-free diet | Gluten-reduced diet (50 mg per day) | Gluten-reduced diet (1000 mg per day) | "Normal" diet (10 g gluten/day) |
|---|---|---|---|---|
| Protein degradation | ↑ | ↑ | ↑ | ↑ |
| Carbohydrate metabolism | ↑ | ↑ | ↑ | ↑ |

Table 2: Comparison of PICRUSt2-predicted metabolic functions of fecal 16S rRNA microbiome data from healthy adults receiving one capsule per day of a probiotic composition (*Lactobacillus plantarum* DSM 33363, *Lactobacillus plantarum* DSM 33364, *Lactobacillus paracasei* DSM 33373, *Lactobacillus reuteri* DSM 33374, *Bacillus megaterium* DSM 33300, *Bacillus pumilus* DSM 33297, and *Bacillus pumilus* DSM 33355) versus placebo capsules. Verum and placebo capsules were consumed on the background of diets with controlled content of gluten (gluten-free, or 50 mg gluten or 1 g gluten per day) as shown in FIG. 1 "↑" displays significantly increased abundance of the predicted metabolic function in the probiotic group as compared to the placebo group; conversely for "↓".

LITERATURE

1. Feng, Q.; Chen, W. D.; Wang, Y. D. Gut Microbiota: An Integral Moderator in Health and Disease. *Front Microbiol* 2018, 9, 151, doi: 10.3389/fmicb.2018.00151.
2. Schink, M.; Konturek, P. C.: Tietz, E.; Dieterich, W.; Pinzer, T. C.: Wirtz, S.; Neurath, M. F.; Zopf, Y. Microbial patterns in patients with histamine intolerance. *J Physiol Pharmacol* 2018, 69, doi: 10.26402/jpp.2018.4.09.
3. Akobeng, A. K.; Singh, P.; Kumar, M.; Al Khodor, S. Role of the gut microbiota in the pathogenesis of coeliac disease and potential therapeutic implications. *Eur J Nutr* 2020, 59, 3369-3390, doi: 10.1007/s00394-020-02324-y.
4. Verdu, E. F.; Galipeau, H. J.; Jabri, B. Novel players in coeliac disease pathogenesis: role of the gut microbiota. *Nat Rev Gastroenterol Hepatol* 2015, 12, 497-506, doi: 10.1038/nrgastro.2015.90.
5. De Angelis, M.; Vannini, L.; Di Cagno, R.; Cavallo, N.; Minervini, F.; Francavilla, R.; Ercolini, D.; Gobbetti, M. Salivary and fecal microbiota and metabolome of celiac children under gluten-free diet. *Int J Food Microbiol* 2016, 239, 125-132, doi: 10.1016/j.ijfoodmicro.2016.07.025.
6. D'Argenio, V.; Casaburi, G.; Precone, V.; Pagliuca, C.; Colicchio, R.; Sarnataro, D.; Discepolo, V.; Kim, S. M.; Russo, I.; Del Vecchio Blanco, G., et al. Metagenomics Reveals Dysbiosis and a Potentially Pathogenic *N. flavescens* Strain in Duodenum of Adult Celiac Patients. *Am J Gastroenterol* 2016, 111, 879-890, doi: 10.1038/ajg.2016.95.
7. Esposito, M. V.; Nardelli, C.; Granata, I.; Pagliuca, C.; D'Argenio, V.; Russo, I.; Guarracino, M. R.; Salvatore, P.; Del Vecchio Blanco, G.; Ciacci, C., et al. Setup of Quantitative PCR for Oral *Neisseria* spp. Evaluation in Celiac Disease Diagnosis. *Diagnostics* (*Basel*) 2019, 10, doi: 10.3390/diagnostics10010012.
8. Iaffaldano, L.; Granata, I.; Pagliuca, C.; Esposito, M. V.; Casaburi, G.; Salerno, G.; Colicchio, R.; Piccirillo, M.; Ciacci, C.; Del Vecchio Blanco, G., et al. Oropharyngeal microbiome evaluation highlights *Neisseria* abundance in active celiac patients. *Sci Rep* 2018, 8, 11047, doi: 10.1038/s41598-018-29443-1.
9. Panelli, S.; Capelli, E.; Lupo, G. F. D.; Schiepatti, A.; Betti, E.; Sauta, E.; Marini, S.; Bellazzi, R.; Vanoli, A.; Pasi, A., et al. Comparative Study of Salivary, Duodenal, and Fecal Microbiota Composition Across Adult Celiac Disease. *J Clin Med* 2020, 9, doi: 10.3390/jcm9041109.
10. Caminero, A.; McCarville, J. L.; Galipeau, H. J.; Deraison, C.; Bernier, S. P.; Constante, M.; Rolland, C.; Meisel, M.; Murray, J. A.; Yu, X. B., et al. Duodenal bacterial proteolytic activity determines sensitivity to dietary antigen through protease-activated receptor-2. *Nat Commun* 2019, 10, 1198, doi: 10.1038/s41467-019-09037-9.
11. Galipeau, H. J.; McCarville, J. L.; Huebener, S.; Litwin, O.; Meisel, M.; Jabri, B.; Sanz, Y.; Murray, J. A.; Jordana, M.; Alaedini, A., et al. Intestinal microbiota modulates gluten-induced immunopathology in humanized mice. *Am J Pathol* 2015, 185, 2969-2982, doi: 10.1016/j.ajpath.2015.07.018.

12. De Angelis, M.; Siragusa, S.; Vacca, M.; Di Cagno, R.; Cristofori, F.; Schwarm, M.; Pelzer, S.; Flugel, M.; Speckmann, B.; Francavilla, R., et al. Selection of Gut-Resistant Bacteria and Construction of Microbial Consortia for Improving Gluten Digestion under Simulated Gastrointestinal Conditions. *Nutrients* 2021, 13, doi: 10.3390/nu13030992.
13. Caminero, A.; Galipeau, H. J.; McCarville, J. L.; Johnston, C. W.; Bernier, S. P.; Russell, A. K.; Jury, J.; Herran, A. R.; Casqueiro, J.; Tye-Din, J. A., et al. Duodenal Bacteria From Patients With Celiac Disease and Healthy Subjects Distinctly Affect Gluten Breakdown and Immunogenicity. *Gastroenterology* 2016, 151, 670-683, doi: 10.1053/j.gastro.2016.06.041.
14. Wacklin, P.; Laurikka, P.; Lindfors, K.; Collin, P.; Salmi, T.; Lahdeaho, M. L.; Saavalainen, P.; Maki, M.; Matto, J.; Kurppa, K., et al. Altered duodenal microbiota composition in celiac disease patients suffering from persistent symptoms on a long-term gluten-free diet. *Am J Gastroenterol* 2014, 109, 1933-1941, doi: 10.1038/ajg.2014.355.
15. Leccioli, V.; Oliveri, M.; Romeo, M.; Berretta, M.; Rossi, P. A New Proposal for the Pathogenic Mechanism of Non-Coeliac/Non-Allergic Gluten/Wheat Sensitivity: Piecing Together the Puzzle of Recent Scientific Evidence. *Nutrients* 2017, 9, doi: 10.3390/nu9111203.
16. Transeth, E. L.; Dale, H. F.; Lied, G. A. Comparison of gut microbiota profile in celiac disease, non-celiac gluten sensitivity and irritable bowel syndrome: A systematic review. *Turk J Gastroenterol* 2020, 31, 735-745, doi: 10.5152/tjg.2020.19551.
17. Garcia-Mazcorro, J. F.; Rivera-Gutierrez, X.; Cobos-Quevedo, O. J.; Grube-Pagola, P.; Meixueiro-Daza, A.; Hernandez-Flores, K.; Cabrera-Jorge, F. J.; Vivanco-Cid, H.; Dowd, S. E.; Remes-Troche, J. M. First Insights into the Gut Microbiota of Mexican Patients with Celiac Disease and Non-Celiac Gluten Sensitivity. *Nutrients* 2018, 10, doi: 10.3390/nu10111641.
18. Caio, G.; Lungaro, L.; Segata, N.; Guarino, M.; Zoli, G.; Volta, U.; De Giorgio, R. Effect of Gluten-Free Diet on Gut Microbiota Composition in Patients with Celiac Disease and Non-Celiac Gluten/Wheat Sensitivity. *Nutrients* 2020, 12, doi: 10.3390/nu12061832.
19. Kaminski, M.; Skonieczna-Zydecka, K.; Nowak, J. K.; Stachowska, E. Global and local diet popularity rankings, their secular trends, and seasonal variation in Google Trends data. *Nutrition* 2020, 79-80, 110759, doi: 10.1016/j.nut.2020.110759.
20. Niland, B.; Cash, B. D. Health Benefits and Adverse Effects of a Gluten-Free Diet in Non-Celiac Disease Patients. Gastroenterol Hepatol (N Y) 2018, 14, 82-91.
21. Dieterich, W.; Schuppan, D.; Schink, M.; Schwappacher, R.; Wirtz, S.; Agaimy, A.; Neurath, M. F.; Zopf, Y. Influence of low FODMAP and gluten-free diets on disease activity and intestinal microbiota in patients with non-celiac gluten sensitivity. *Clin Nutr* 2019, 38, 697-707, doi: 10.1016/j.clnu.2018.03.017.
22. Hansen, L. B. S.; Roager, H. M.; Sondertoft, N. B.; Gobel, R. J.; Kristensen, M.; Valles-Colomer, M.; Vieira-Silva, S.; Ibrugger, S.; Lind, M. V.; Maerkedahl, R. B., et al. A low-gluten diet induces changes in the intestinal microbiome of healthy Danish adults. *Nat Commun* 2018, 9, 4630, doi: 10.1038/s41467-018-07019-x.
23. Francavilla, R.; Piccolo, M.; Francavilla, A.; Polimeno, L.; Semeraro, F.; Cristofori, F.; Castellaneta, S.; Barone, M.; Indrio, F.; Gobbetti, M., et al. Clinical and Microbiological Effect of a Multispecies Probiotic Supplementation in Celiac Patients With Persistent IBS-type Symptoms: A Randomized, Double-Blind, Placebo-controlled, Multicenter Trial. *J Clin Gastroenterol* 2019, 53, e117-e125, doi: 10.1097/MCG.0000000000001023.
24. Lilja, S.; Stoll, C.; Krammer, U.; Hippe, B.; Duszka, K.; Debebe, T.; Hofinger, I.; Konig, J.; Pointner, A.; Haslberger, A. Five Days Periodic Fasting Elevates Levels of Longevity Related Christensenella and Sirtuin Expression in Humans. *Int J Mol Sci* 2021, 22, doi: 10.3390/ijms22052331.
25. Klindworth, A.; Pruesse, E.; Schweer, T.; Peplies, J.; Quast, C.; Horn, M.; Glockner, F. O. Evaluation of general 16S ribosomal RNA gene PCR primers for classical and next-generation sequencing-based diversity studies. *Nucleic Acids Res* 2013, 41, e1, doi: 10.1093/nar/gks808.
26. Caporaso, J. G.; Kuczynski, J.; Stombaugh, J.; Bittinger, K.; Bushman, F. D.; Costello, E. K.; Fierer, N.; Pena, A. G.; Goodrich, J. K.; Gordon, J. I., et al. QIIME allows analysis of high-throughput community sequencing data. *Nat Methods* 2010, 7, 335-336, doi: 10.1038/nmeth.f.303.
27. Edgar, R. C. Search and clustering orders of magnitude faster than BLAST. *Bioinformatics* 2010, 26, 2460-2461, doi: 10.1093/bioinformatics/btq461.
28. Douglas, G. M.; Maffei, V. J.; Zaneveld, J. R.; Yurgel, S. N.; Brown, J. R.; Taylor, C. M.; Huttenhower, C.; Langille, M. G. I. PICRUSt2 for prediction of metagenome functions. *Nat Biotechnol* 2020, 38, 685-688, doi: 10.1038/s41587-020-0548-6.

The invention claimed is:

1. A method for treating or preventing dysbiosis in humans and animals, the method comprising:

administering a preparation to a human or animal in need thereof, wherein the preparation comprises probiotic strains *Lactobacillus plantarum* DSM 33363, *Lactobacillus plantarum* DSM 33364, *Lactobacillus paracasei* DSM 33373, *Lactobacillus reuteri* DSM 33374, *Bacillus megaterium* DSM 33300, *Bacillus pumilus* DSM 33297, and *Bacillus pumilus* DSM 33355, wherein administration of the preparation results, relative to a placebo, in:

(i) an increase in alpha and/or beta diversity of the gut microbiota, and (ii) an increase in protein degradation and carbohydrate metabolism capacity of the gut microbiome.

2. The method according to claim 1, wherein the preparation is used for the modulation of the composition and activity of gut microbiota, the method comprising at least one selected from the group consisting of:

a) the preparation leads to an increase of taxa belonging to *Bifidobacterium, Lactobacillus, Akkermansia muciniphila, Streptococcus, Faecalibacterium prausnitzii,* b) the preparation leads to a decrease of taxa belonging to Proteobacteria, *Neisseria, Neisseria flavescens, Escherichia coli, Bordetella, Shigella, Salmonella, Bacteroides, Prevotella, Helicobacter pylori, Yersinia, Pseudomonas, Pseudomonas aeruginosa, Klebsiella*, and c) the preparation leads to an increased alpha or beta diversity of the gut microbiota of at least 5% relative to placebo.

3. The method according to claim 1, wherein the probiotic strains *Lactobacillus plantarum* DSM 33363, *Lactobacillus plantarum* DSM 33364, *Lactobacillus paracasei* DSM 33373, *Lactobacillus reuteri* DSM 33374, *Bacillus megaterium* DSM 33300, *Bacillus pumilus* DSM 33297, and *Bacillus pumilus* DSM 33355 lead to an increased protein degradation and carbohydrate metabolism capacity of the gut microbiome of humans and animals as determined by predictive functional profiling of fecal microbiome samples.

4. The method according to claim 1, wherein the probiotic strains *Lactobacillus plantarum* DSM 33363, *Lactobacillus plantarum* DSM 33364, *Lactobacillus paracasei* DSM 33373, *Lactobacillus reuteri* DSM 33374, *Bacillus megaterium* DSM 33300, *Bacillus pumilus* DSM 33297, and *Bacillus pumilus* DSM 33355 are present in a dormant form or as vegetative cells.

5. The method according to claim 1, wherein the preparation further comprises one or more further probiotic strains.

6. The method according to claim 1, wherein the preparation further comprises one or more selected from the group consisting of: microbial proteases purified from *Aspergillus niger, Aspergillus oryzae, Bacillus* sp., *Lactobacillus* sp., *Pediococcus* sp., *Weissella* sp., *Rothia mucilaginosa, Rothia aeria*, subtilisins, nattokinase, arabinoxylans, barley grain fibre, oat grain fibre, rye fibre, wheat bran fibre, inulins, fructooligosaccharides (FOS), galactooligosaccharides (GOS), resistant starch, beta-glucans, glucomannans, galactoglucomannans, guar gum, xylooligosaccharides, and alginate.

7. The method according to claim 1, wherein the preparation is for treating or preventing gluten-related disorders.

8. The method according to claim 1 for treating or preventing dysbiosis that derives from adhering to a special dietary practice including gluten-free diets, diets with reduced intake of gluten or cereals or cereal-derived or cereal-containing food stuffs.

9. The method according to claim 1 for treating or preventing dysbiosis related to obesity, non-alcoholic fatty liver disease, allergic diseases, major depressive disorder, Parkinson's disease, Alzheimer's disease, or auto-immune diseases.

10. The method according to claim 1, further comprising a substance, which acts as a permeabilizer of the microbial cell membrane of members of *Bacillus* sp., *Lactobacillus* sp., *Pediococcus* sp. and *Weissella* sp.

11. The method according to claim 1, wherein one or more probiotic strains selected from the group consisting of *Bacillus* sp., *Lactobacillus* sp., *Pediococcus* sp. and *Weissella* sp. are immobilized individually or together.

12. The method according to claim 1, wherein the preparation is a food or feed supplement or functional food or food product or pharmaceutical product.

13. The method according to claim 12, wherein said preparation is formulated for oral use, is formulated as syrup or beverage, or is added to food.

14. The method according to claim 1, wherein the preparation further comprises *Pediococcus pentosaceus* DSM 33371.

15. The method according to claim 7, wherein the gluten-related disorders are selected from the group consisting of celiac disease, non-celiac gluten sensitivity, wheat allergy, and gluten-sensitive irritable bowel syndrome in a subject or animal in need thereof.

16. The method according to claim 1, wherein the dysbiosis is dysbiosis related to type two diabetes.

17. The method according to claim 10, wherein the substance is alginate.

18. The method according to claim 13, wherein the oral use is pills, capsules, tablets, granular powders, opercula, soluble granules, bags, or drinkable vials.

19. The method according to claim 13, wherein the food is cereals, gummies, bread, muesli, muesli bars, health bars, biscuits, chocolates, yoghurts, or spreads.

* * * * *

SEQUENCE LISTING

```
Sequence total quantity: 2
SEQ ID NO: 1            moltype = DNA  length = 19
FEATURE                 Location/Qualifiers
source                  1..19
                        mol_type = other DNA
                        organism = synthetic construct
SEQUENCE: 1
gagtttgatc ntggctcag                                          19
```

-continued

```
SEQ ID NO: 2            moltype = DNA  length = 18
FEATURE                 Location/Qualifiers
source                  1..18
                        mol_type = other DNA
                        organism = synthetic construct
SEQUENCE: 2
gtnttacngc ggckgctg                                          18
```